United States Patent
Kiraly et al.

(10) Patent No.: US 10,643,401 B2
(45) Date of Patent: May 5, 2020

(54) TWO-DIMENSIONAL CINEMATIC MEDICAL IMAGING IN COLOR BASED ON DEEP LEARNING

(71) Applicant: Siemens Healthcare GmbH, Erlangen (DE)

(72) Inventors: Atilla Peter Kiraly, San Jose, CA (US); Kaloian Petkov, Lawrenceville, NJ (US); Jin-hyeong Park, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 39 days.

(21) Appl. No.: 16/295,072

(22) Filed: Mar. 7, 2019

(65) Prior Publication Data

US 2019/0206144 A1 Jul. 4, 2019

Related U.S. Application Data

(62) Division of application No. 15/677,460, filed on Aug. 15, 2017, now Pat. No. 10,282,918.

(Continued)

(51) Int. Cl.
*G06T 19/20* (2011.01)
*G06T 11/00* (2006.01)
(Continued)

(52) U.S. Cl.
CPC ............ *G06T 19/20* (2013.01); *A61B 5/7425* (2013.01); *G06N 3/0454* (2013.01); *G06N 20/00* (2019.01); *G06T 11/001* (2013.01); *H04N 1/6027* (2013.01); *G06T 2200/08* (2013.01); *G06T 2207/10016* (2013.01); *G06T 2207/10024* (2013.01); *G06T 2207/10072* (2013.01);
(Continued)

(58) Field of Classification Search
CPC ..... G06T 19/20; G06T 11/001; A61B 5/7425; G06N 3/0454; G06N 99/005; H04N 1/6027
See application file for complete search history.

(56) References Cited

U.S. PATENT DOCUMENTS 7,505,037 B2 3/2009 Wang
7,616,199 B2 11/2009 Engel
(Continued)

FOREIGN PATENT DOCUMENTS

JP 2000105838 A 4/2000
WO WO0243008 A1 5/2002

OTHER PUBLICATIONS

Cheng, Zezhou, Qingxiong Yang, and Bin Sheng. "Deep colorization." Proceedings of the IEEE International Conference on Computer Vision. 2015.
(Continued)

*Primary Examiner* — David F Dunphy (57) ABSTRACT

A 2D medical image is colorized. In one approach, a deep-learnt classifier is trained to colorize from color 2D medical images. The color 2D medical images for training are cinematically rendered from slabs to add color. In another approach, a deep machine-learnt generator creates slices as if adjacent to the 2D medical image. The slices and 2D medical image form a slab, which is cinematically rendered to add color. The result is a colorized 2D medical image.

19 Claims, 6 Drawing Sheets
(5 of 6 Drawing Sheet(s) Filed in Color)

Related U.S. Application Data (60) Provisional application No. 62/397,214, filed on Sep. 20, 2016.

(51) Int. Cl.
*A61B 5/00* (2006.01)
*G06N 20/00* (2019.01)
*G06N 3/04* (2006.01)
*H04N 1/60* (2006.01)

(52) U.S. Cl.
CPC ............ *G06T 2207/10081* (2013.01); *G06T 2207/10088* (2013.01); *G06T 2207/20084* (2013.01); *G06T 2210/41* (2013.01); *G06T 2219/2012* (2013.01); *Y04S 10/54* (2013.01)

(56) References Cited

U.S. PATENT DOCUMENTS

| | | | | |
|---|---|---|---|---|
| 9,020,217 | B2* | 4/2015 | Amyot | G06T 19/00 382/128 |
| 2006/0153434 | A1 | 7/2006 | Wang | |
| 2008/0292194 | A1 | 11/2008 | Schmidt | |
| 2009/0136106 | A1 | 5/2009 | Roberts | |
| 2010/0128950 | A1 | 5/2010 | Woods | |
| 2012/0078102 | A1 | 3/2012 | Lee | |
| 2012/0245465 | A1 | 9/2012 | Hansegard | |
| 2013/0335434 | A1* | 12/2013 | Wang | G06T 15/506 345/581 |
| 2014/0294138 | A1 | 10/2014 | Jerebko | |
| 2016/0171157 | A1* | 6/2016 | Mielekamp | G06F 19/321 345/589 |
| 2016/0267703 | A1 | 9/2016 | Zhou | |
| 2017/0003366 | A1 | 1/2017 | Jafari-Ihouzani | |
| 2017/0200269 | A1* | 7/2017 | Reicher | G16H 30/20 |
| 2017/0262978 | A1* | 9/2017 | Reynolds | A61B 5/055 |

OTHER PUBLICATIONS

Chung, Audrey G., et al. "Discovery Radiomics for Multi-Parametric MRI Prostate Cancer Detection." arXiv preprint arXiv:1509.00111 (2015).

Comaniciu et al: "Shaping the future through innovations: From medical imaging to precision medicine"; Medical Image Analysis, vol. 33, pp. 19-26.

European Partial Search Report dated Feb. 6, 2018 in corresponding European application No. 17191897.2.

Extended European Search Report (EESR) dated May 16, 2018 in corresponding European Patent Application No. 17191897.2.

Kerr, J. P., et al. ""True" color surface anatomy: mapping the Visible Human to patient-specific CT data" Computerized medical imaging and graphics 24.3 (2000): 153-164.

Pappa, et al: "Cinematic rendering—an alternative to volume rendering for 3D computed tomography imaging"; Insights Into Imaging, vo 1.7, No. 6, Sep. 15, 2016 (Sep. 15, 2016), pp. 849-856.

Shah, Ami A., G. Mikita, and Kalpesh M. Shah. "Medical image colorization using optimization technique." (2013).

Siemens Medical Imaging "Pictures of the Future" The Magazine for Research and Innovation—https://www.siemens.com/innovation/en/home/pictures-of-the-future/health-and-well-being/medical-imagingcinematic- vrt.html.

Zhang, Richard, Phillip Isola, and Alexei A. Efros. "Colorful image colorization." European Conference on Computer Vision. Springer International Publishing, 2016.

* cited by examiner

FIG. 12

TWO-DIMENSIONAL CINEMATIC MEDICAL IMAGING IN COLOR BASED ON DEEP LEARNING

RELATED APPLICATIONS

The present patent document is a divisional application of U.S. patent application Ser. No. 15/677,460, filed Aug. 15, 2017, which claims the benefit of the filing date under 35 U.S.C. § 119(e) of Provisional U.S. Patent Application Ser. No. 62/397,214, filed Sep. 20, 2016, which are hereby incorporated by reference.

BACKGROUND

The present embodiments relate to medical imaging. Two-dimensional medical imaging is performed in color.

Figure 1:
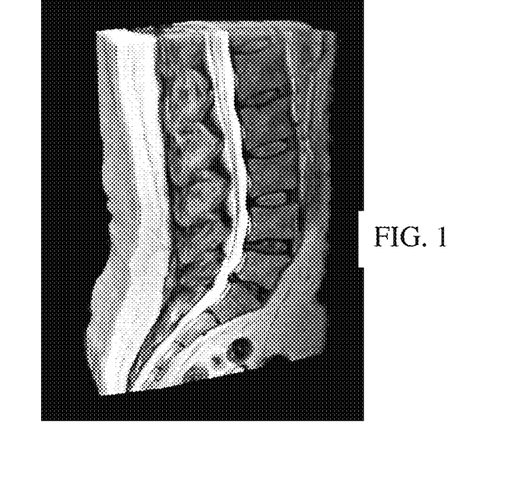
FIG. 1 is an example 3D rendered color image from a slab.

To better communicate findings, radiologists may create volume renderings of findings. Cinematic rendering creates realistic renderings from volumes or three-dimensional (3D) scan data. Such renderings vividly demonstrate anatomy and findings to both patients and referring physicians. Compared to the traditional volume rendering approaches, the cinematic renderer computes a physically-based light transport that mimics real-world light behavior and allows for special effects typically associated with photorealism (accurate shadows, ambient occlusions, color bleeding, accurate camera lens simulation, etc.). These effects improve the spatial understanding of 3D structure from a single image, whereas simpler renderers may require user interaction with the data to obtain the same level of understanding. FIG. 1 shows a cinematic rendering of a slab (volume with greater extent along two dimensions than the third) from a MR volume of the lower spine. The 3D rendering adds color using a look-up table while light transport simulation accounts for shadows, occlusions and color bleeding from nearby structures.

With a two-dimensional (2D) MR dataset, 3D renderings are not possible by traditional volume or cinematic rendering. Frequently, in common Computed Tomography (CT), Magnetic Resonance Imaging (MR), Fluoroscopy, or Ultrasound (US) examinations, the data contains limited or no 3D volume information. As an example, an MR image of the spine uses detailed 2D views at specific locations instead of 3D volumes. Any volume rendering method, including the cinematic renderer, is ineffective or limited when confronted with strictly 2D data. MR, CT, and US generate black and white images (e.g., grayscale images). Color mappings may be used instead of grayscale. The radiologist may not be able to communicate findings in a way more easily understood by the patient or physician due to the lack of color or with color that does not appear natural. 3D rendering cannot be used to add color to 2D data.

SUMMARY

By way of introduction, the preferred embodiments described below include methods, systems, instructions, and computer readable media for colorizing a 2D medical image. In one approach, a deep-learnt classifier is trained to colorize from color 2D medical images. The color 2D medical images for training are rendered with a cinematic renderer from 3D slabs to add color. In another approach, a deep machine-learnt generator creates slices as if adjacent to the 2D medical image. The slices and 2D medical image form a slab, which is cinematically rendered to add color. The result is a colorized 2D medical image.

In a first aspect, a method is provided for training a deep machine-learnt classifier for colorizing a two-dimensional medical image. Training data representing volumes (e.g., 3D distributions of measures) of multiple patients is loaded into memory. The volumes include scalar values from medical scanning of the patients. Slabs, each representing multiple slices in each of the volumes, are isolated. The scalar values of the slabs are three-dimensionally color rendered to two-dimensional color images with cinematic rendering. The two-dimensional color images are used to train a deep machine-learnt classifier with deep machine learning to colorize the two-dimensional medical image.

In a second aspect, a method is provided for colorizing a two-dimensional medical image of a patient. A deep machine-learnt generator generates a first two-dimensional slice representing a first plane based on input of the two-dimensional medical image. A slab of the first two-dimensional slice and the two-dimensional medical image is formed. A renderer color renders the slab with a cinematic renderer. The slab as rendered in color is displayed as a colorized version of the two-dimensional medical image.

In a third aspect, a system is provided for two-dimensional cinematic medical imaging. A medical scanner is configured to scan a first plane of a patient and generate scan data for the first plane. A machine is configured to output scan data for a second plane by application of the scan data for the first plane to a deep-machine-learnt extrapolator. A graphics processing unit is configured to cinematically render a color image of the first plane from a slab formed from the scan data of the first plane and the scan data of the second plane. A display is configured to display the color image.

In a fourth aspect, a system is provided for colorizing two-dimensional medical imaging. A medical scanner is configured to scan a first plane of a patient and generate scan data for the first plane. A machine is configured to output a color image from the scan data for the first plane by application of the scan data for the first plane to a deep-machine-learnt colorizer trained from cinematic renderings of slabs. A display is configured to display the color image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Deep learning and cinematic rendering are used for colorizing 2D medical images. A 2D medical image of the human body is taken as input and a colorized 2D image is produced as output. In one approach, the deep-machine-learnt extrapolator extrapolates nearby slices to the input 2D medical image. The extrapolated slices and input image form a thin 3D volume, to which cinematic volume rendering produces a color rendered image. The colors applied to the image may be based on colors obtained from volume renderings.

In another approach, deep machine learning is trained to colorize the input 2D medical image. Deep machine learning may be used to colorize photographs. Unfortunately, the same approach is difficult to directly apply to medical images. The colors and textures of photographs have little relation to medical images. Additionally, the ground truth for the colors is not immediately available or feasible to generate for medical images whereas color photographs are readily available for training. Cinematic rendering of thin slabs is used to generate the ground truth for the deep learning.

Instead of using cinematic rendering to create the training images, real-world sectioned anatomical images of the whole body from a database (e.g., see Visible Human, Visible Korean, etc., projects) or from actual humans (e.g., cadaver or biopsy). The training images may come from a full body project like the Visible Human, or they can be patient- and organ-specific anatomical images with and without pathologies. This extends the photograph-based learning where the machine learns to color in a way emulating an actual appearance for human tissue based on the sectional images. In other words, a correspondence between the scanning modality (CT/MR) and the physical appearance of the tissue is made by the trained colorizer. The training teaches the colorizer to add color based on camera or sectional color images, and the colorizer is then applied to 2D images from a scanning modality.

A machine learning-based approach incorporates information from cinematic rendering, such as intensity, texture, and/or spatial information. The various approaches for colorizing are based on the concept of enhancing 2D medical images for better understanding. The methods provide realistic images with 2D medical data. The colors may be used to help differentiate abnormalities in the tissues. This capability allows for improved communications between the radiologist and referring physicians or patients. The color information may be further used for radiomics in a "non-presumptive" manner.

Figure 2:
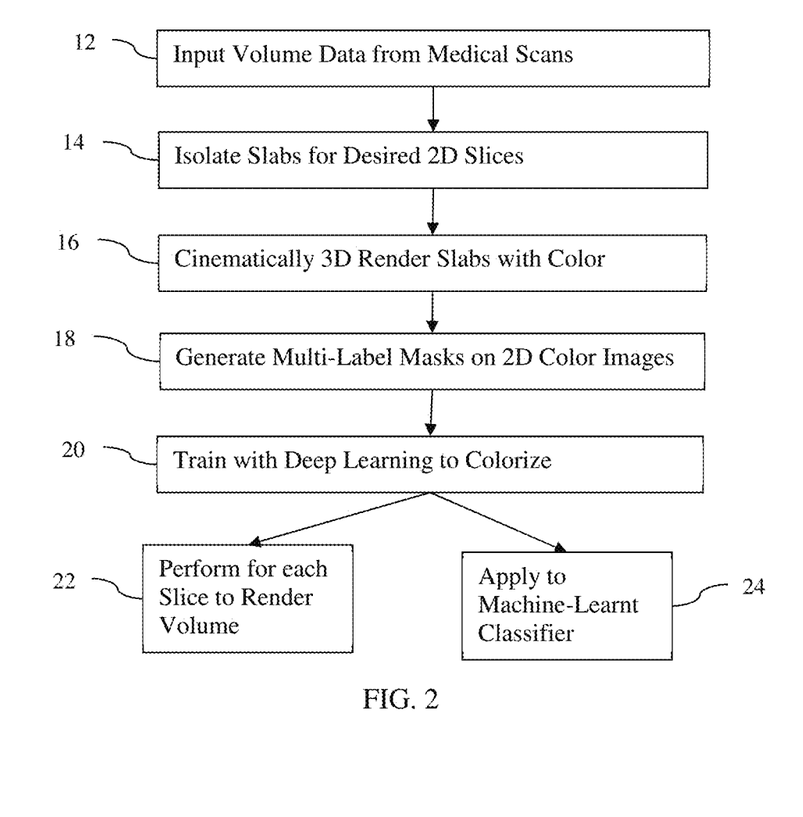
FIG. 2 is a flow chart diagram of one embodiment of a method for training a deep machine-learnt classifier for colorizing a 2D medical image.

FIG. 2 shows one embodiment of a method for training a deep machine-learnt classifier for colorizing a 2D medical image. Colored ground truth data is generated by cinematic rendering of slabs. The resulting color images from the slabs are used as ground truth 2D medical images to train a network to color 2D medical images. Using the resulting deep-learnt network, an input 2D medical image is colorized. Realistic colors and light effects result.

Figure 3:
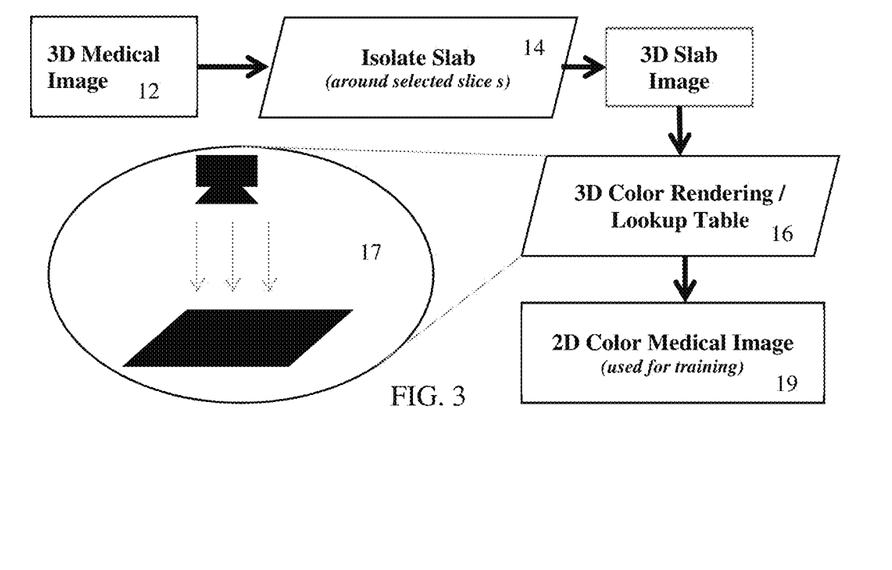
FIG. 3 is a flow chart diagram of another embodiment of the method for training the deep machine-learnt classifier for colorizing the 2D medical image.

FIG. 3 shows another embodiment of the method. FIG. 3 represents acts 12-16 and 20 of FIG. 2. FIGS. 2 and 3 are described together below.

The methods of FIGS. 2 and 3 are implemented by a processor and a graphics processing unit in a server, computer, or other machine. In one embodiment, the system of FIG. 12 implements the method of FIG. 1 or 2, with or without the medical imager 56 and/or display 54. For example, data is input by loading from a memory, a processor performs the generation of the training data and the machine training based on the data, and the memory stores the learnt artificial intelligence. As another example, the medical scanner and/or memory input the data to a server, which performs slab isolation and the training. For application, a different medical scanner, computer, server, or other processor applies the machine-learnt classifier to colorize an input 2D image.

The acts are performed in the order shown (top to bottom or numerical) or another order. For example, segmentation of act 18 is performed after act 12 or after act 14 and before act 16. The input volume data or 2D images are segmented, and then the 3D slabs are created in act 14. For each slab, a 2D image is rendered, taking into account the segmentation mask (e.g., for areas segmented as tumor or broken bone, increase brightness, change rendering material properties, etc). The colored 2D image, where the color accounts for the segmentation, is used to train the network.

Additional, different, or fewer acts may be provided. For example, act 18, act 22, and/or act 24 are not provided. As another example, acts for application of the colorizer are provided. In yet another example, acts for selecting the training data, configuring the rendering, and/or configuring the training are provided.

In act 12, volume data is input. The volume data is used to create training data for machine learning, so is training data. Since colorized ground truth information is not typically available for 2D medical images, volume data is used to create the colorized ground truth. The volume data itself may not be input for training, but is input to extract the training data.

The volume data is gathered from one or more memories, sensors, and/or scanners. The gathered data may be stored and/or transmitted to a buffer, memory, cache, processor, or other device.

Many samples of the same type of data are input. To learn statistical or other relationships that may be sufficiently complex that a human cannot perceive the relationships at a same level, tens, hundreds, or thousands of samples are provided. Each sample is a volume. Since thin slabs are used to generate the ground truth, one volume may be used to generate a plurality of colorized 2D medical images. Fewer volumes may be needed to provide the samples.

Any volume data may be used. The volume data is scan data from scanning one or more patients. For each sample, the scan data represents a patient. The same region of the patient is represented in each volume, such as a joint or organ.

The volume data represents a 3D region. The volume data is in any format, such as a scan format (e.g., polar coordinate), interpolated to a regular or irregular grid, and/or a reconstructed object. For volume data formatted as on a Cartesian grid, the volume data covers an N×M×O region where N, M, and O are integers greater than 1, such as N=M=O=64, 128, 254, or 508 (e.g., 254×254×254). N, M, and O may not be equal (e.g., 128×254×254).

3D or volume data is different than 2D data. 2D data represents just a plane. The 3D data may be formed from a stack of 2D frames of data. 3D data represents a volume or more than just the plane. A slice is a plane or data representing just a plane. The slice may or may not correspond to a 2D scan region, such as a slice being an arbitrary plane in a volume. Scalar values of the volume may be interpolated to the slice.

For machine training, the goal or ground truth information is input with the sample input data. In this case, the ground truth is color 2D medical images. The volume data and any 2D slice are scalar values, such as measurements from medical scanning. For US, the scalar values represent intensity of acoustic return. For MR, the scalar values represent T1, T2, or other measures of magnetic response. For CT, the scalar values represent density or x-ray attenuation. The scalar values are of any resolution, such as being 4, 8, or 16 bit values. The scalar values do not include color information, such as not including red, green, blue (RGB) information or having RGB values that are substantially equal (e.g., +/−5%). Acts 14 and 16 are directed to providing ground truth in the form of color 2D medical images for training.

In an alternative embodiment, the input data are a set of 2D images representing just planes. Rather than isolating slabs by selecting subsets in act 14, the planar information is extrapolated into 3D slabs.

In act 14, the processor isolates slabs. The isolation is by membership, such as labeling locations or planar slices as being part of a slab. Alternatively, the isolation is by extracting the scalar values and forming separate slab representations in memory.

Each slab represents multiple slices in a volume. The slab is a subset of the volume. For example, the volume is 64×64×64. A thin slab includes two-seven slices of the volume, such as 3×64×64. More slices may be used. The slab is 3D, but less than all the volume. The slab may be at any orientation relative to the volume. Interpolation may be used to form the scalar values at the orientation of the slab.

Any number of slabs may be formed from each volume. The same slice may be used in multiple slabs, such as using a moving window defining the slabs. In one embodiment, all of the volume is divided into overlapping or non-overlapping slabs of parallel slices with the slabs parallel to each other. In other embodiments, only parts of the volume are used. For example, image processing is applied to identify one or more slices of interest. Slices representing only planes in the volume are selected automatically, but manual or semi-automatic selection may be used. Adjacent slices are then selected to form a corresponding one or more slabs. Two to four or other number of adjacent slices (i.e., immediately adjacent to the slice of interest or a selected slice) representing only planes are identified and included in the slab. Other nearby (e.g., within 3 grid points) slices than adjacent slices may be included. The slab is formed of the selected slice and adjacent and/or nearby slices.

The slabs are isolated to make use of slab renderings using the cinematic renderer to provide a color basis for the ground truth. By isolating one or more slabs for the multiple volumes, tens, hundreds, or thousands of slabs are identified from volumes of patients.

In act 16, a renderer 3D renders the scalar values of the slabs to 2D color images. The rendering collapses the 3D slabs, which represent multiple planes, to a 2D color image. Where a few planes are included the slab and the camera position for rendering views the slab orthogonally or substantially orthogonally to the slab, the 3D rendered 2D color image is similar to a 2D color image of a single plane. Substantially accounts for +/−10 degrees. The rendering collapses the 3D distribution of scalar values to a 2D distribution for display on a 2D display device. The variation in the scalar values in the depth or third dimension may alter or result in a different pixel value than having just 2D data for imaging.

Each slab is rendered. By rendering the tens, hundreds, or thousands of slabs, a same number of color 2D images are provided. By altering rendering settings and re-rendering any number of slabs, different color 2D images may be provided. Any rendering settings may be used. In one embodiment, rendering settings appropriate for the application (e.g., examination for a particular organ, lesion, joint, and/or tissue) are used.

The renderer is a physically-based renderer for cinematic rendering. The physically-based renderer is a graphics processing unit, array of graphics processing units, workstation, server, computer, or other machine capable of the required light simulation. Any physically-based rendering algorithm capable of computing the light transport may be used, such as path tracing, unbiased path tracing, Monte-Carlo path tracing, or Metropolis light transport. The physically-based rendering simulates the physics of light propagation (e.g., probability of absorption, scattering, and/or passage of many photons, resulting in accumulation of light interaction along different probability-based paths) to create an image. Cinematic rendering is different than accumulating volume samples with local illumination along viewing rays from the camera, as is done for traditional volume rendering. In path tracing implemented for physically-based rendering, the paths of light or photons, including due to scattering and absorption, are modeled and used for rendering. The physically-based rendering result is built up over time as the rendering relies on probabilistic scattering and tracing millions of light paths.

The cinematic rendering uses a transfer function including a color look-up table. The look-up table relates the scalar values to colors. Due to the path tracing, the colors vary based on the light interaction of surrounding locations. The color is based on more than mere look-up of a color with a value since the interaction of light with surrounding locations influences the light at a given location. Using a cinematic renderer, the lookup table and rendering properties are first setup for a particular 3D medical image application or a set of similar 3D images.

The cinematic rendering results in a photorealistic image. A sequence of images may be provided as the image is built or rendered (i.e., as more and more traced light paths are added). Alternatively, for a given set of values of rendering parameters, a single image is output. FIG. 1 shows an example of cinematic rendering of a thick slab (e.g., tens of slices) with a given color look-up table.

As shown in FIG. 3 (see 17), the rendering is performed with the camera positions spaced from and viewing orthogonal or substantially orthogonal to the slab. The selected slice and adjacent or nearby slices are rendered with an orthographic projection camera set facing the slab so that each pixel in the rendering matches that of the original slab. The result is a 1-1 match of color image 19 that also contains specular components and other effects based upon the tissue intensity and texture. Due to use of cinematic rendering, the output 2D color medical images may include certain specular or other lighting effects applied to textures that would not be possible to create using a lookup table relating pixel scalar values to color without rendering.

In act 18, a multi-label mask is generated. A multi-label mask is generated for each of all or a subset of the 2D color images. The multi-label mask labels different parts of the color images, such as segmenting one or more organs or types of tissue. Alternatively or additionally, annotations label. Any labeling indicating content of the image other than the colorized pixels may be used. Different regions are specified or assigned different labels.

Findings in 2D medical images are documented by a radiologist but may not be readily apparent to patients or referring physicians. Direct annotations, such as arrows, help localize findings, but the medical image itself may still be cryptic to non-radiologists. For example, an X-Ray image of the knee may show injuries that are readily apparent to the consulted radiologist but perhaps the subtleties are not appreciated by the referring physician or their patient. To improve effective communication of the image and its findings, the multi-label mask is used as an input into the coloring of the deep machine-learnt colorizer. Realistic yet clearly differentiated coloring may greatly assist in visual communications of the findings. The colorizer may learn to color differently based on the multi-label mask information.

In another embodiment, the medical image segmentation is performed on the input data from act 12 prior to performing act 16. The masks or annotations are input to the cinematic renderer to render the training images. The cinematic rendering alters the color, transfer function, or other setting by location (pixel) based on the segmentation.

Figure 6:
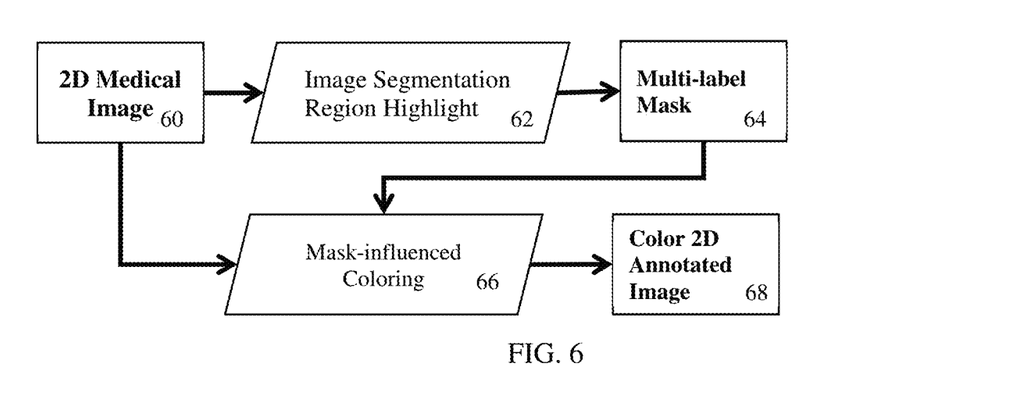
FIG. 6 is a flow chart diagram of one embodiment of colorizing using multi-label mask information.

FIG. 6 shows an example approach. Acts 60-68 may be performed for generating the training data. The coloring of act 66 is by the cinematic renderer, such as rendering differently by region based on the labels of the mask. In alternative or additional embodiments, acts 60-68 are performed as part application where the coloring of act 66 is performed by the deep machine-learnt colorizer.

Each 2D medical image 60, with or without color, is input for segmentation or creation 62 of the multi-label mask. Different regions are highlighted in the sense of being labeled differently, resulting in the multi-label mask 64. The processor automatically generates the multi-label mask. As an example, the seed-based Random Walker algorithm is used to mark different regions of the image. Alternatively, manual or semi-automatic generation may be used. For example, the user segments or marks different regions or findings of the image to create a multi-label mask. The coloring in act 66 is based, at least in part, on the mask 64. For example, different shading, colors, brightness, and/or other color characteristic are used for different regions or segments. As a result, the color 2D image 68 includes coloring responsive to the mask. The annotations of the mask may or may also be included in the image 68.

Referring again to FIG. 2, the collection of color 2D medical images generated from rendering thin slabs are used to train a deep machine-learnt classifier in act 20. The tens, hundreds, or thousands of sample color 2D medical images are used to learn how to assign color to a grayscale input 2D medical image. The artificial intelligence or intelligences are machine trained. The collected samples, including ground truth color images and the starting 2D grayscale images (e.g., center or another slice of the thin slabs), are used to train. A machine, such as a processor, computer, server, or other device learns from the samples. Using machine-learning, complex statistical relationships between large numbers (e.g., tens, hundreds, thousands, or more) of input variables to any number of output variables are extracted from the large number of samples.

The training is for imaging in any context. One model may be learned for any number of imaging situations. Alternatively, different models are trained for different situations. The different situations may include different scan modalities (e.g., different model for CT, MR, or US. The different situations may include different types of tissue of interest (e.g., liver versus kidney), different diagnostic purpose or workflow (e.g., cancerous lesion versus bone calcification), and/or different users (e.g., different operators may have different preferences for visualization).

Any now known or later developed machine learning may be used. Regression, classification, and/or reinforcement learning are used. Neural network, Bayes network, or support vector machine training may be used. Hierarchal or other approaches may be used. Unsupervised, supervised, or semi-supervised machine learning may be used.

To train, features are extracted from the input data. Haar wavelet, steerable, or other features may be extracted from the images of the training data. Alternatively, the input data itself (e.g., scalar values of the scan dataset) is used. For deep learning, the machine learns features as part of the training. For example, deep learning (e.g., deep structured learning, hierarchical learning, or deep machine learning) models high-level abstractions in data by using multiple processing layers with structures composed of multiple non-linear transformations, where the input data features are not engineered explicitly as in shallow learning algorithms. Deep learning figures out the data features that end up providing a good colorizer. Deep learning extracts high level abstractions (features) from low level input data (e.g., raw images) that is suitable for the trained task, so may be more convenient than and superior to hand-crafted features.

Figure 5:
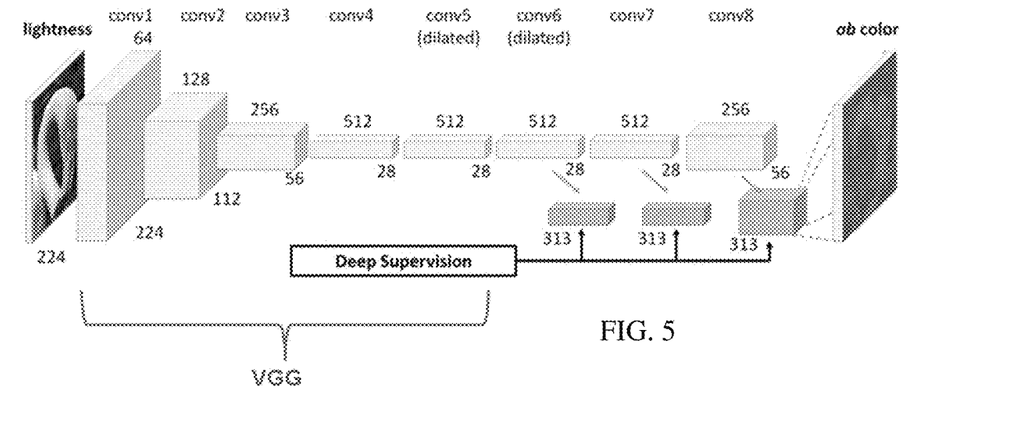
FIG. 5 is an example neural network for learning to colorize.

A deep neural network processes the input via multiple layers of feature extraction to produce features used to derive output colors. FIG. 5 shows one example convolutional neural network for deep learning. This deep network includes eight convolutional layers, including two dilatational layers. Other numbers of layers and/or types of layers may be used. The first five layers form a visual geometry group and the last three layers provide feedback for supervising the deep learning. Other deep learnt, sparse auto-encoding models may be trained and applied. The machine training is unsupervised in learning the features to use and how to classify given an input sample (i.e., feature vector). The deep supervision provides feedback automatically to determine the best features given the ground truth. The deep learning analyzes textures and intensities to learn to derive color estimates.

Through training, the machine learns a matrix representing the deep machine-learnt classifier for colorizing an input grayscale 2D medical image. The ground truth color 2D medical images guide the training. Training such a network to color medical images may be difficult due to a lack of realistically colored 2D medical data. Using the color training data created by the 3D cinematic renderer provides the ground truth for learning to colorize. The learning may use details, such as specular components on musculature, to color images.

The convolutional neural network is trained from only the input training samples. Alternatively, a deep learning using photographs is initially performed, providing a starting point. The training photographs are color and black and white. The photographs may or may not be photographs of patients or tissue. This existing network or a portion thereof may be used as a starting point (e.g., using the node weights) for training on medical images from imagers or scanners for scanning the interior of the patient. The subsequent training is based on the color 2D medical images from the cinematic rendering.

In one embodiment of FIG. 6, the training includes training to color with the multi-label masks. The training data includes the multi-label masks. Once the multi-labeled mask is available, the labeled regions may each be processed differently. Different weighted networks may be trained with different characteristics, such as normal, bright, glowing, and/or shiny. The label of the mask decides the coloring style for that location. For example, an injured muscle in a 2D MRI is labeled to be colored glowing to especially highlight that muscle. In another implementation, a single deep-learning colorizer is trained to color differently based on the mask labeling. Each label in the mask is used to color the image in a unique fashion by using custom rules embedded in a machine-learnt pipeline to color each label differently.

Once trained, the deep machine-learnt colorizer (renderer) receives as input a 2D medical image. Scalar values representing just a plane or without representing a third dimension are input to the matrix or matrices of the deep machine-learnt colorizer. The deep machine-learnt colorizer outputs, in response to the input, a colorized 2D medical image. Based on the training data created through cinematic rendering of thin slabs, the colorizer is trained. In application, the colorizer applies color to the input 2D medical image without 3D rendering. The colorized 2D medical image may more intuitively or in a more recognizable way indicate differences or characteristics of the organ or tissue.

Figure 4:
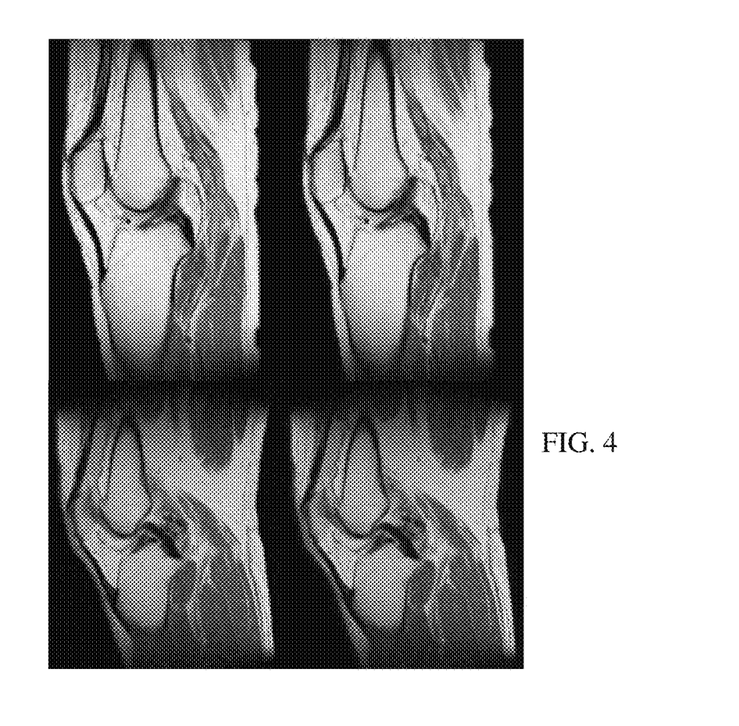
FIG. 4 shows four example images including two input MR 2D images and the resulting colorized versions by application of a trained color classifier.

FIG. 4 demonstrates some realistic colorings possible with deep learning from cinematic renderings of grayscale scalar values in thin slabs. 2D grayscale images of MR slices of two different views of a knee are input to the deep machine-learnt colorizer. The left side of FIG. 4 shows the input grayscale images. The colorizer outputs a 2D colored medical image. The right side of FIG. 4 shows the output colorized images. The effects and color image features shown in the color images of FIG. 4 are based on the color training data from cinematic rendering, so are not possible by a simple color lookup table assigning different scalar values to color. For example, the color effects in the muscle tissue respond to texture and other context highlighted due to use of learning to color from cinematic renderings. Compared to black and white images, the color images may be more efficient for communication and reporting in general.

In another embodiment for application, the trained colorizer is used to allow 3D rendering using any type of rendering in act 22. The deep machine-learnt classifier is applied to individual slices representing only planes in a new volume representing a patient. Color is applied slice-by-slice to an entire volume to define the colors. The individual colorized slices are assembled into a color volume. The color volume is then 3D rendered using any type of rendering.

Figure 7:
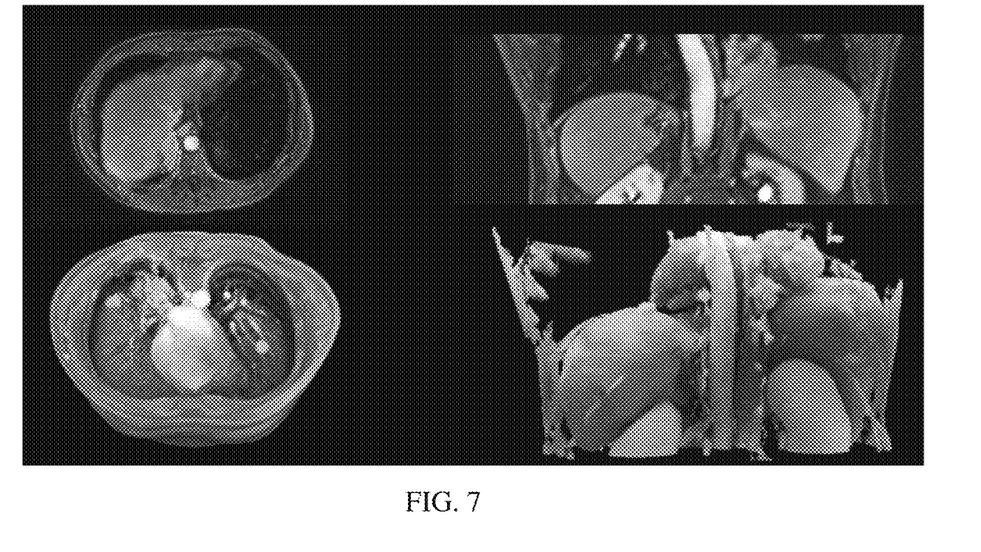
FIG. 7 shows four example images using a machine-learnt color classifier to colorize slices of a volume, which is then rendered using any type of rendering.

FIG. 7 shows example colorized images. The upper row shows colorized 2D images applied to CT slices. The lower row shows images rendered with 3D cinematic rendering from stacks of colored slices fused back into a volume and rendered. Subtle lines of different colors are observed in the lower right image due to changes in the slices. This artifact may be resolved by blending the colored slices across different slicing planes. The lower two images demonstrate how the proposed method may be used to provide color assignments to 3D data. Other rendering from the colored volume may be used, such as ray casting, alpha blending, volume rendering, or surface rendering.

In another embodiment represented in FIG. 2, the results of application of the deep machine-learnt colorizer to a 2D medical image are applied to a further machine-learnt classifier in act 24. The further machine-learnt classifier may be trained as part of the neural network in the deep learning. The learnt colors are used to make further classification about the input 2D medical image. Alternatively, the further machine-learnt classifier is a separate classifier, such as another deep machine-learnt classifier, a support vector machine, or a Bayesian network.

The further machine-learnt classifier is trained to classify a diagnostic or therapeutic characteristic based on an input of the colorized version of the 2D medical image. "Radiomics" uses machine-learnt classifiers to identify and create image features that may not be visible to the naked eye and that correlate to a specific outcome or therapy prediction. For example, certain textures in tumors in CT data are indicative of tumor malignancy.

The features are created and correlated based on a set of data with known outcomes. Frequently, it is difficult for a human viewer of a 2D image to recognize these features, so machine training is used. The feature correlation is originally established with a set of labeled training data, especially in the case of deep learning. In a "non-presumptive" approach, the coloring of the image is not based on a labeled training dataset of previous tumor outcomes. This is "non-presumptive" radiomics since the raw image data is directly colored according to a non-biased network trained on colored images. Slight changes in the tumor texture or shape may result in dramatic changes in the determined colors. By machine training, the color information may be used to classify the diagnosis or prognosis for the patient.

Figure 8:
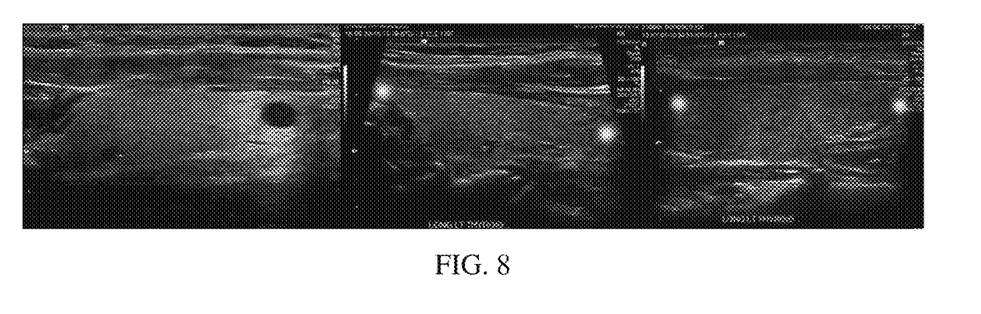
FIG. 8 shows example colorized versions of ultrasound images.

FIG. 8 shows three colorized 2D US images of the thyroid. All images are of the same body region, but from different patients. Although the texture of the images appears similar when viewed natively (black and white), coloring produces different results due to subtle differences in context (e.g., intensity variation or texture). The coloring is not biased towards any particular patient outcome or diagnosis. Another classifier receives the distinctive color information and outputs a diagnosis or prognosis using "non-presumptive" radiomics.

In the embodiment where the further classifier is trained as part of or linked to training of the colorizer, the colorizer is trained to output specific colors depending on diagnosis or prognosis of a tumor. The input to the trained classifier is one or more grayscale 2D medical images for the patient. Images across multiple time points, such as over days or weeks with or without one or more intervening treatments, are input. The trained network has a multi-channel input with a different channel for each time or 2D image. The temporal information may be indicative of characteristics of the tumor indicating a given prognosis or diagnosis.

Figure 9:
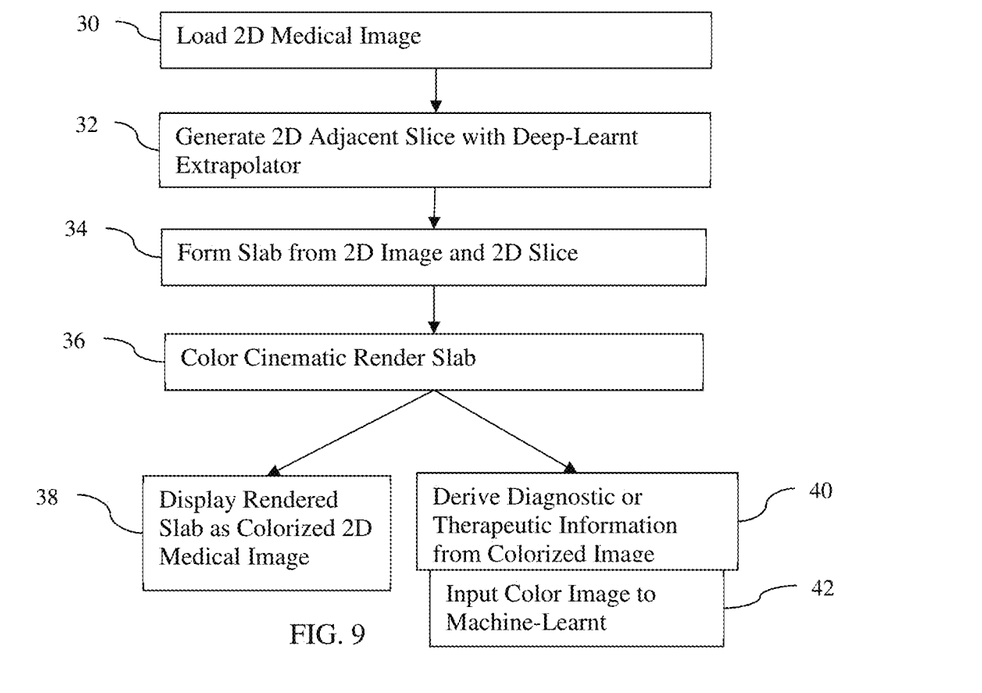
FIG. 9 is a flow chart diagram of one embodiment of a method for colorizing a 2D medical image.

In the approach of FIG. 1, cinematic rendering of data from previous patients is used to create training data so that a deep machine-learnt colorizer may be trained to directly colorize an input 2D medical image for a current patient. FIG. 9 shows another approach where cinematic rendering is used to colorize the input 2D medical image for the current patient. FIG. 9 shows one embodiment of a method for colorizing a two-dimensional medical image of a patient. Realistic colored images are obtained from 2D datasets using physically-based volume rendering of a thin-slab. The approach used to generate labeled color data in FIG. 2 is, in a way, reversed to color a 2D image. The deep machine learning is used to train an extrapolator to extrapolate one or more additional slices given an input slice. Since the input 2D image cannot be rendered directly, the deep machine-learnt extrapolator provides slices to form a thin slab for a 3D rendering.

Figure 10:
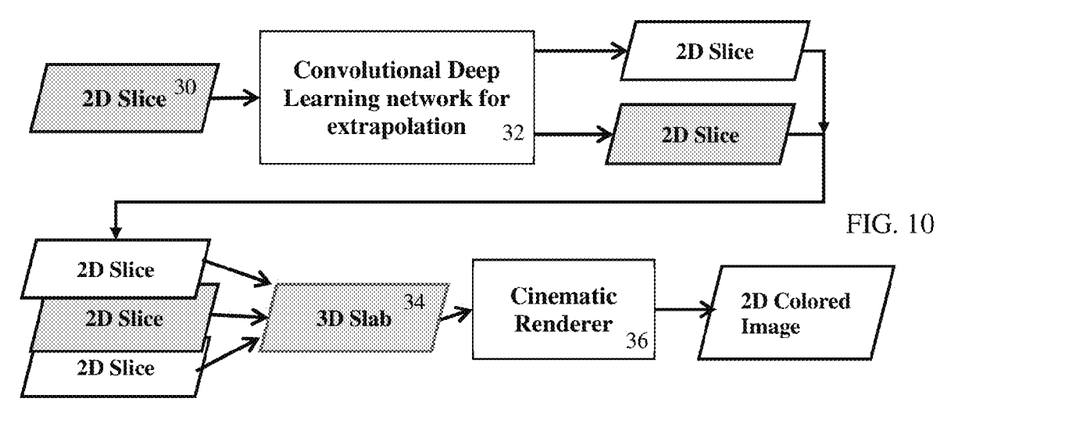
FIG. 10 is a flow chart diagram of another embodiment of the method for colorizing the 2D medical image.
Figure 11:
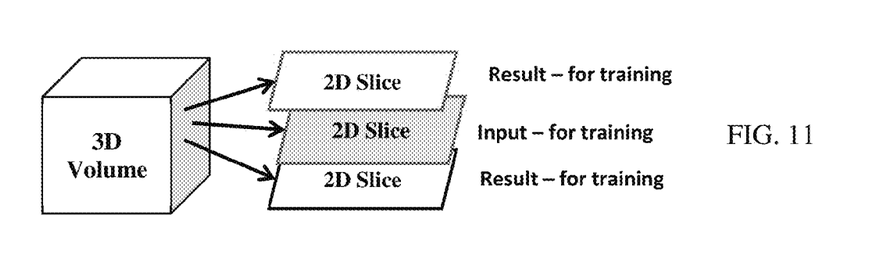
FIG. 11 is a flow chart diagram of data selection for training a deep machine-learnt extrapolator for generating slices for the methods of FIGS. 9 and 10.

FIG. 10 shows another embodiment of the method of FIG. 9. FIGS. 9 and 10 are directed to application using a deep machine-learnt extrapolator. FIG. 11 is directed to training the deep machine-learnt extrapolator. The extrapolator is trained to generate one or more 2D slices given an input 2D medical image. The trained extrapolator is then used to generate slices to form a slab with the input 2D medical image, allowing cinematic rendering of the constructed 3D slab to generate a colored 2D image. This approach offsets the coloring of the image to the lookup table and methods used in the cinematic renderer.

This method may be used to produce training data for the direct deep learning to colorize of the methods of FIGS. 2 and 3. The resultant slab rendering of the method of FIGS. 9 and 10 may be performed with a slight (e.g., +/−20 degree) perspective view. Such view options are not possible with the method of FIGS. 2 and 3 since the deep machine-learnt colorizer directly converts into a color image on a pixel-to-pixel basis.

The acts of FIGS. 9 and 10 are performed with a processor, such as a computer, server, medical scanner, or workstation. In one embodiment, acts 30-34 are performed by processor of a computer, workstation or medical scanner. Act 36 is performed by a graphics processing unit, such as a plurality of graphics cards. Acts 38-42 are performed by the processor with or without a display device.

The acts are performed in the order shown or another order. Additional, different, or fewer acts may be used. For example, acts 38-42 are not performed. As another example, act 30 is not performed as a transmission of the 2D medical image is received without loading from memory.

In act 30, a 2D medical image is loaded from a memory, sensors, and/or other source. A medical scanner may provide the frame of data for the image, such as a medical dataset representing just a plane of the patient. Medical information from a picture archiving and communications server may be obtained. Any source may be used. Image is used to represent scan data that may be processed to form an image, data for a currently or previously displayed image, or other imaging related frame of data representing spatial distribution of return or measured signals from the patient.

The medical data is for a given patient. While the training may use samples from many patients to learn to generate one or more slices, the learnt model is applied to the medical data for a patient to output one or more slices for that patient. The same or different machine-learnt models are applied to data for any number of patients.

For application, the 2D medical image is scan data representing a 2D slice. Other slices or 3D data is not available. For the training of FIG. 11, volumes are used. The volume or slab data provides multiple slices. The training learns to generate adjacent or nearby slices based on input of a given single slice. Many samples of slices and adjacent or nearby slices as the ground truth are used to learn. For unsupervised training, the training data is extracted from a 3D volume. Given 3D volumes, any slices are selected as the starting or input 2D image. The adjacent slices are selected as expected outputs from the extrapolation network (i.e., ground truth). Since this task requires no manual supervision, a large set of training data may be collected automatically. Manual selection may be used.

In act 32, a processor implementing a deep machine-learnt extrapolator generates one or more 2D slices representing adjacent or nearby planes. This deep machine-learnt generator creates the 2D slices based on input of the 2D medical image. The generated slices are of planes different than the plane of the input 2D medical image. The planes are parallel, but may be non-parallel. In one embodiment, one or two 2D slices are generated as adjacent slices on each side of an input 2D medical image. In an alternative embodiment, the deep machine-learnt extrapolator generates the slab directly without separate generation of 2D slices.

The generated slices or slab are of scalar values for different pixels or spatial locations. The scalar values do not include color information. Alternatively, the scalar values only include grayscale information (e.g., RGB values all being equal or within 5% of each other in the dynamic range).

Any machine learning and corresponding machine-learnt classifier may be used. In one embodiment, a deep machine-learnt generator is a trained convolutional deep learnt neural network. For example, a convolutional network deep learning architecture based on VGG-19 or other architectures may be used to output the nearby slices. Deep learning may learn to generate 2D images from an input 2D image, but with variations due to being offset in space. The 2D image is input into the extrapolating deep learning network, producing nearby slices. Textural details in 3D are extracted and imparted into nearby slices. Additionally, shape changes of well-defined objects, such as certain bones and organs, may be predicted in nearby slices.

In the multi-label embodiment of FIG. 6, the 2D medical image being input includes or is processed to create the multi-label mask 64. The slices generated by the extrapolator are generated with corresponding masks. Due to variation in the shapes of organ or tissue in other slices, the extrapolator may be trained to include multi-label masking in the generated slices. The generated slices include generated multi-label masks.

In act 34 of FIGS. 9 and 10, the processor generates a thin slab. The input 2D image and the generated adjacent or nearby slices are grouped together, creating a thin slab. Any number of slices may be included, such as 2-4 slices in addition to the input 2D image. The slices and input 2D image are stacked. The generated slices may have specific positions relative to the input 2D image, so the stack incorporates the ordering. This grouping forms a volume or data representing a 3D distribution of spatial locations. The resultant extrapolated slices are combined with the original slice to form a thin slab that is used as input for the renderer. Once the network is trained, given a 2D medical image, the corresponding slices are extrapolated and formed into a 3D slab.

For medical use cases, the slab should be thin so that any later clinical decision is not biased by the additional slices computed. Thin may be five or fewer parallel slices. Thicker slabs may be used.

In act 36, a renderer (e.g., graphics processor) color renders the slab formed in act 34. Cinematic rendering is applied to the slab. The 3D rendering uses path tracing or other simulation of light transport to render to a 2D display or image. The rendering uses a look-up table linking scalar values with colors and the light interaction from adjacent locations to assign the color to a given pixel in the rendering. The color is responsive to the surrounding texture. Unlike the input 2D image, the slab is a type of volume that may be rendered with the cinematic renderer. To create a color 2D medical image based on the input 2D medical image, the camera view for the rendering faces the slice of the input 2D image (i.e., is orthogonal to the slab) or is slightly off axis with a perspective depending upon the effect desired.

Where the generated slices and/or input 2D image include multi-label masks, the cinematic rendering may use the label information to control colorization. Lighting effects may be altered or different for different regions designated by the multi-label masks. The labeled regions may each be processed differently. Different render characteristics, such as normal, bright, glowing, or shiny, may be applied for rendering. The label of the mask then decides the rendering style for that location. For example, an injured muscle in a 2D MRI may be labeled to be rendered glowing to especially highlight that muscle. In another implementation, the rendering provides for some locations to be brighter based on the label.

In act 38, the rendered 2D image from the thin slab is displayed on a display device. The 3D rendering creates a 2D color medical image. Since a thin slab with view angle substantially orthogonal to the slab is used, the rendered 2D image of the slab is displayed as a colorized version of the input 2D medical image. Since the renderer generates the 2D image with color, the input 2D medical image is provided with color. A colorized version of the input 2D medical image is output to the display.

In act 40, the colorized version of the 2D medical image is used for radiomics. The color 2D medical image is input to a machine-learnt classifier in act 42. In act 40, the machine-learnt classifier outputs, based on the input, a diagnostic or therapeutic classification. The machine-learnt classifier uses the color information with or without other input features to diagnose or predict outcome. The color information may be input directly or features may be extracted from the color and other image information. For a deep machine-learnt classifier, the color 2D medical image is input and learnt features are convolved with the image to determine the output.

The approaches for colorizing an input 2D medical image of FIGS. 2 and 3 or FIGS. 9 and 10 may be used for various applications. The colorization may assist in presenting findings in non-volumetric imaging. For example, in lower spine examinations, high-resolution 2D MR images are taken at sagittal views of the spine at specific locations. 3D volumetric imaging is avoided since 3D imaging may result in an overall lower resolution at the plane of interest and take additional time to acquire. The resultant 2D data slices limit the communications of findings between the radiologist and referring physician or patient to a single black and white or grayscale image. The proposed methods allow for a realistic color 2D image to be presented, improving communication and therefore value of the radiologist. Note that with traditional volume rendering approaches, simple presentation may not be possible due to the 2D nature of the data. In addition, simply using a lookup table to colorize does not color based on textural and higher-level features of the image.

In another example application, radiomics based on color information for non-volumetric imaging is provided. In the case of MR images of the liver, slight variations in texture and appearance may create more drastic changes in color. By ensuring a similar scanning protocol, these subtle changes may be more visible to the radiologist. The coloring may correspond to different levels of tumor therapy effectiveness or tumor types. Color is applied regardless or independent of any diagnostic or prognostic consideration. The coloring may allow for better detection of subtle changes in the images, such as by a machine-learnt classifier. The color images may be better compared to each other to show changes over time. Alternatively, the coloring is based on diagnostic or prognostic consideration. If the deep machine-learnt network for colorizing is trained against tumor types or treatment, the network may also serve as a graphical way to communicate established correlations and as a statistical feature for outcome decisions.

Figure 12:
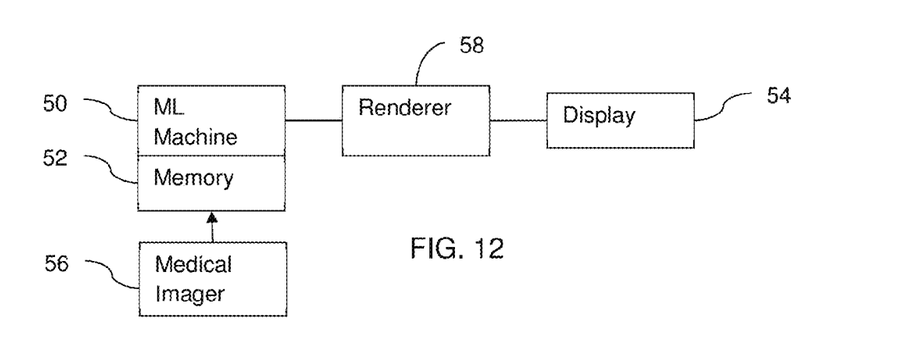
FIG. 12 is a block diagram of one embodiment of a system for colorizing 2D medical images.

FIG. 12 shows a block diagram of one embodiment of a system for two-dimensional cinematic medical imaging. The system is for training with machine learning and/or application of a machine-learnt model. Using deep learning, the system learns to provide slices to form a slab for 3D rendering to add color or learns to colorize based on training data from 3D color rendering.

The system implements the method of FIGS. 2, 3, 6, 9, 10, and/or 11. Other methods or acts may be implemented which combine cinematic rendering and deep machine learning or a deep machine learnt classifier to provide a color 2D medical image based on an input non-color, 2D only image.

The system includes a machine 50, a memory 52, a display 54, a medical imager 56, and a renderer 58. Additional, different, or fewer components may be provided. For example, the medical imager 56 and/or memory 52 are not provided. In another example, a network or network connection is provided, such as for networking with a medical imaging network or data archival system. A user interface, such as a user input device (e.g., mouse, trackball, touch pad, and/or keyboard), may be provided for interacting with the machine 50, renderer 58, or other components.

The machine 50, memory 52, renderer 58, and/or display 54 are part of the medical imager 56. Alternatively, the machine 50, memory 52, renderer 58, and/or display 54 are part of a server, workstation, or computer separate from the medical imager 56. The machine 50, memory 52, renderer 58, and/or display 54 are a personal computer, such as desktop or laptop, a workstation, a server, a network, or combinations thereof. In yet other embodiments, the machine 50 and memory 52 are part of a separate computer from the renderer 58.

The medical imager 56 is a medical diagnostic imaging system. US, CT, x-ray, fluoroscopy, positron emission tomography (PET), single photon emission computed tomography (SPECT), and/or MR systems may be used. The medical imager 56 may include a transmitter and includes a detector for scanning or receiving data representative of the interior (e.g., just a plane or a volume) of the patient. The medical imager 56 acquires scan data representing the patient. For training, the scan data may represent a volume or just a plane of the patient. For application, the scan data represents just a plane of the patient.

In alternative embodiments, the medical imager 56 is not provided, but a previously acquired dataset (e.g., 2D image) for a patient is stored in the memory 52. In yet other alternatives, many medical images and/or 3D volumes are provided in the memory 52 as the training data.

The machine 50 is a computer, workstation, server, processor, or other device configured to apply machine learning and/or to apply a machine-learnt model. The machine 50 is configured by software, hardware, and/or firmware. For learning, the machine 50 is configured by one or more machine learning algorithms. For applying a learnt model, the machine 50 is configured, in part, by a learnt matrix or matrices associating input data to output values.

The machine 50 applies a machine-learnt model, such as one learnt with deep learning. The machine-learnt model, as implemented by the machine 50, generates input features and/or outputs based on application of medical data from a scan of a patient. In one embodiment, the machine is configured to output a color image from input of grayscale 2D image or scan data. The 2D scan data is input to a deep-machine-learnt colorizer trained from cinematic renderings of and orthogonal to thin slabs. The output is a color image for the same plane represented by the input 2D scan data. In another embodiment, the output in response to input of the 2D scan data is one or more sets of scan data representing other planes and/or a surrounding slab. A deep machine-learnt extrapolator generates a 3D slab from the input 2D scan data.

The memory 52 is a graphics processing memory, a video random access memory, a random-access memory, system memory, cache memory, hard drive, optical media, magnetic media, flash drive, buffer, database, combinations thereof, or other now known or later developed memory device for storing training data, values for rendering settings, color look-up tables, 2D images, colorized 2D images, and/or other information. The memory 52 is part of the medical imager 56, part of a computer associated with the machine 50, part of a computer associated with the renderer 58, a database, part of another system, a picture archival memory, or a standalone device.

The memory 52 or other memory is alternatively or additionally a non-transitory computer readable storage medium storing data representing instructions executable by the programmed machine 50 for learning or applying the machine-learnt model, for cinematic rendering, for masking, for diagnosis or prognosis prediction, or for other process. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The renderer 58 is a graphics processing unit, graphics card, graphic chip, multi-core processor, or other processor for running a software package that implements the cinematic rendering (e.g., path tracing or physically-based rendering). The renderer 58 is configured by an application programming interface to render an image from the 3D scan data representing a patient. Using physically-based rendering, a photorealistic image is rendered. In one embodiment, cinematic rendering is used to generate color images from 3D thin slabs for training with deep learning to colorize 2D images. In another embodiment, the graphics processing unit is configured to cinematically render a color image of a plane from a slab formed from the scan data of the plane and scan data for other planes extrapolated by a deep machine-learnt extrapolator.

The display 54 is a monitor, LCD, projector, plasma display, CRT, printer, or other now known or later developed device for displaying the color image or images. The display 54 receives images from the machine 50, memory 52, renderer 58, or medical imager 56. The color images of the tissue captured by the medical imager 56 are displayed. Rather than or in addition to displaying a grayscale 2D image of the patient, a colorized or color 2D image is displayed. Other information may be displayed as well, such as generated graphics (e.g., for the multi-label mask), text, or quantities as a virtual overlay.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for colorizing two-dimensional medical imaging, the system comprising:
    a medical scanner configured to scan a first plane of a patient and generate scan data for the first plane;
    a machine configured to output a color image from the scan data for the first plane by application of the scan data for the first plane to a deep-machine-learnt colorizer trained from cinematic renderings of slabs; and
    a display configured to display the color image.

2. The system of claim 1 wherein the deep-machine-learnt colorizer was trained from the cinematic renderings of slabs each having been isolated as multiple slices from volumes for other patients.

3. The system of claim 1 wherein the deep-machine-learnt colorizer was trained from the cinematic renderings comprising color renderings of three-dimensional distributions of scalar values to two-dimensional color images.

4. The system of claim 1 wherein the deep-machine-learnt colorizer was trained from the cinematic renderings comprising renderings with unbiased path tracing.

5. The system of claim 1 wherein the deep-machine-learnt colorizer was trained from the cinematic renderings rendered with a camera oriented substantially orthogonally to the slabs.

6. The system of claim 1 wherein the deep-machine-learnt colorizer comprises a convolutional neural network.

7. The system of claim 1 wherein the deep-machine-learnt colorizer was trained with scalar values of one of multiple slices of each slab as input images and the two-dimensional color images as ground truth.

8. The system of claim 1 wherein the machine is configured to output other color images from scan data of other planes in a volume of the patient, assemble the color image and other color images into a color volume, and rendering from the color volume.

9. The system of claim 1 wherein the machine is configured to classify a diagnostic or therapeutic characteristic based on an input of the color image to a machine-learnt classifier.

10. The system of claim 1 wherein the deep-learnt-colorizer is configured to output the color image based on input of a multi-label input mask.

11. The system of claim 1 wherein the deep-learnt-colorizer was trained from the cinematic renderings of slabs including one or more slices generated by a deep machine-learnt generator.

12. A method for colorizing two-dimensional medical imaging, the method comprising:
   scanning a first plane of a patient, the scanning resulting in scan data for the first plane;
   generating a color image from the scan data, the generating being by a deep-machine-learnt colorizer trained from cinematic renderings of slabs; and
   displaying the color image.

13. The method of claim 12 wherein generating comprises generating by the deep-machine-learnt colorizer having been trained from the cinematic renderings comprising renderings with unbiased path tracing.

14. The method of claim 12 wherein generating comprises generating by the deep-machine-learnt colorizer having been trained from the cinematic renderings rendered with a camera oriented substantially orthogonally to the slabs.

15. The method of claim 12 wherein generating comprises generating by the deep-machine-learnt colorizer comprising a convolutional neural network.

16. The method of claim 12 further comprising generating other color images from scan data of other planes in a volume of the patient, assembling the color image and other color images into a color volume, and rendering from the color volume.

17. The method of claim 12 further comprising classifying a diagnostic or therapeutic characteristic based on an input of the color image to a machine-learnt classifier.

18. The method of claim 12 wherein generating comprises generating in response to input of the scan data and a multi-label input mask to the deep-machine-learnt colorizer.

19. The method of claim 12 wherein generating comprises generating by the deep-learnt-colorizer having been trained from the cinematic renderings of slabs including one or more slices generated by a deep machine-learnt generator.

* * * * *